United States Patent
Garcia Fabrega et al.

(10) Patent No.: US 10,239,684 B2
(45) Date of Patent: Mar. 26, 2019

(54) DEVICE AND METHOD FOR DIFFUSING VOLATILE SUBSTANCES

(71) Applicant: ZOBELE ESPAÑA, S.A., Barcelona (ES)

(72) Inventors: Ruben Garcia Fabrega, Barcelona (ES); Sergio Luque Vera, Barcelona (ES)

(73) Assignee: Zobele Espana, S.A., Barcelona (ES)

( * ) Notice: Subject to any disclaimer, the term of this patent is extended or adjusted under 35 U.S.C. 154(b) by 0 days.

(21) Appl. No.: 15/100,087

(22) PCT Filed: Oct. 29, 2014

(86) PCT No.: PCT/ES2014/070811
§ 371 (c)(1),
(2) Date: May 27, 2016

(87) PCT Pub. No.: WO2015/079084
PCT Pub. Date: Jun. 4, 2015

(65) Prior Publication Data
US 2017/0001789 A1 Jan. 5, 2017

(30) Foreign Application Priority Data
Nov. 27, 2013 (ES) .................................. 201331728

(51) Int. Cl.
*B65D 83/26* (2006.01)
*A61L 9/01* (2006.01)
(Continued)

(52) U.S. Cl.
CPC .............. *B65D 83/262* (2013.01); *A61L 9/01* (2013.01); *A61L 9/14* (2013.01); *G05B 15/02* (2013.01);
(Continued)

(58) Field of Classification Search
CPC .................................................. B65D 83/262
See application file for complete search history.

(56) References Cited

U.S. PATENT DOCUMENTS

| | | | |
|---|---|---|---|
| 4,063,664 | A | 12/1977 | Meetze et al. |
| 5,038,972 | A | 8/1991 | Muderlak et al. |
| (Continued) | | | |

FOREIGN PATENT DOCUMENTS

| | | |
|---|---|---|
| CN | 101394067 A | 3/2009 |
| ES | 256473 U | 10/1981 |
| (Continued) | | |

OTHER PUBLICATIONS

International Search Report dated Dec. 18, 2014 for International Application No. PCT/ES2014/070811.
(Continued)

*Primary Examiner* — Kevin Joyner
(74) *Attorney, Agent, or Firm* — Knobbe, Martens, Olson & Bear, LLP

(57) ABSTRACT

A device for diffusing volatile substances includes a container for the volatile substances, a diffuser configured to diffuse the volatile substances, and at least one battery configured to supply energy to the diffuser. The device also includes a controller detecting data from at least one of the components of the device and determining the period of time during which the at least one battery supplies energy to the diffuser according to the data. This device allows the yield and efficiency to be improved, provides the desired products, and reduces consumption of the batteries.

10 Claims, 2 Drawing Sheets

(51) Int. Cl.
  *A61L 9/14*    (2006.01)
  *G05B 15/02*   (2006.01)
  *H02J 7/00*    (2006.01)
  *B05B 12/02*   (2006.01)

(52) U.S. Cl.
  CPC .......... *H02J 7/0021* (2013.01); *H02J 7/0063* (2013.01); *A61L 2209/11* (2013.01); *A61L 2209/111* (2013.01); *B05B 12/02* (2013.01)

(56) References Cited

U.S. PATENT DOCUMENTS

| | | |
|---|---|---|
| 5,676,283 A | 10/1997 | Wang |
| 5,884,808 A | 3/1999 | Muderlak et al. |
| 2002/0130146 A1* | 9/2002 | Borut ........................ A61L 9/12 222/645 |
| 2005/0139624 A1 | 6/2005 | Hooks et al. |
| 2009/0069749 A1* | 3/2009 | Miller ................ A61M 5/1413 604/151 |

FOREIGN PATENT DOCUMENTS

| | | |
|---|---|---|
| WO | WO 97/12834 A1 | 4/1997 |
| WO | 2005008352 A1 | 1/2005 |

OTHER PUBLICATIONS

Supplementary European Search Report dated Jun. 9, 2017, received in European Patent Application No. EP 14 86 5223.

\* cited by examiner

DEVICE AND METHOD FOR DIFFUSING VOLATILE SUBSTANCES

INCORPORATION BY REFERENCE TO ANY PRIORITY APPLICATIONS

This application is the U.S. National Phase of International Application No. PCT/ES2014/070811, filed Oct. 29, 2014, designating the U.S. and claiming priority to Spain Application No. P201331728, filed Nov. 27, 2013. Any and all applications for which a foreign or domestic priority claim is identified here or in the Application Data Sheet as filed with the present application are hereby incorporated by reference under 37CFR1.57.

FIELD OF THE INVENTION

The present invention relates to a device and method for diffusing volatile substances, particularly to a device and method in which one or more volatile substances are diffused by means of a cell- or battery-powered electrical system.

BACKGROUND OF THE INVENTION

Cell- or battery-powered electrical systems for diffusing volatile substances are known. Electric diffusers are devices for diffusing volatile substances in a closed or outdoor environment by means using electric power, which is used to activate heating elements, diffuser elements or dispensing elements, for the purpose of achieving optimal efficiency, optimal control over the metered amount and optimal control by the user over the dispensing level setting.

Devices of this type are particularly designed for being used without requiring the cooperation of an external air stream, and even without specific temperature restrictions, obtaining good evaporation and/or diffusion of the volatile substances. This obviously does not cancel out the fact that the device is placed in a location where the volatile substance will come into contact with an air flow once it has been released. This will help to diffuse it better in a room, for example, although it does not affect the operation of the apparatus, as described below.

Some of these devices incorporate motors, heaters or electrovalves that allow the vapors to exit through diffuser or dispenser systems, such as nozzles or wicks. These devices comprise a container holding the volatile substance, the electrical system allowing diffusion and the batteries or cells powering the system.

In some cases, the volatile substance is located inside a container in liquid form, and the electrical system is used to dispense metered amounts by means of heating to evaporation, by means of spraying, nebulizing, atomizing or other forms.

In other cases, this container is normally located in a pressurized metal housing acting as protection and support, and including the gas that propels the volatile substance to be diffused. In these cases, diffusion is done automatically by the shut-off valve of the pressurized housing being released at the desired time. This automatic diffusion can be done by means of activating a button, by means of a timer or also by means of an environmental condition sensor (light, movement, bad odors, etc.).

These devices, however, have a series of drawbacks. On one hand, most of them are devices in which the cells have a low service life, which makes it necessary to change the cells often, with the subsequent economic drawback for the user who must change the batteries after replacing the container for the volatile substance a certain number of times.

On the other hand, earlier solutions have an efficiency that is limited by the electrical diffusion system, which does not suitably use the energy from the batteries, wasting a part of it, which ultimately means that many more cells than those strictly required are used, generating waste and an unwanted environmental impact.

It is also the case that some of the preceding solutions not only fail to optimize consumption, but furthermore dispense inconsistent amounts of volatile substance as they do not take into consideration the conditions of the area surrounding the diffusion system.

In many existing solutions, the reason for the energy inefficiency relates directly to the application and/or use of constant time pulses when the diffusion systems are activated and to the fact that the response obtained from cells relates to the charge level of the cells. A very obvious example is the activation of aerosol technology-based diffusion systems, in which the valve of the container holding the substance to be diffused must be pressed with a motor. In these cases, the duration of the pulses is predefined ex factory and constant, so it is calculated for the worst-case conditions of the area surrounding the system (for example, when the voltage level of the batteries is very low, and a long activation time of the motor moving the connecting rod or cam pressing the valve of the container is therefore required). In these cases, when the conditions of the surrounding area are optimal, more than 60% of the energy used for metering can be wasted.

Therefore, the present invention seeks to solve the issues existing in earlier devices, providing a device and a method improving the yield and efficiency, dispensing the desired product amount and reducing consumption of the batteries as much as possible, with the subsequent positive impact on the economic expense and on the environmental impact.

SUMMARY OF THE INVENTION

The aforementioned drawbacks are solved with the device and method for diffusing volatile substances of the invention, having other advantages that will be described below.

According to a first aspect, the device for diffusing volatile substances according to the present invention comprises:

a container for said volatile substances;
diffusion means for diffusing said volatile substances; and
at least one battery for supplying energy to said diffusion means;

and is characterized in that it also comprises control means detecting data from at least one of the components of the device and determining the period of time during which said at least one battery supplies energy to said diffusion means according to said data.

Preferably, said control means detect the voltage and/or current applied to the diffusion means and can also detect the remaining charge in said at least one battery, calculating its expected service life.

It will be clear for a person skilled in the art that when detection of the voltage and/or current applied to the diffusion means is referred to, the intention is to measure the remaining capacity of the batteries or cells for supplying said voltage and/or current, and therefore said voltage and/or current could also be measured indirectly, i.e., anywhere in the electric/electronic circuit, and not just at the level of the diffusion means.

Advantageously, said control means are electronic and/or electric control means.

According to a preferred embodiment, said diffusion means comprise a motor connected to said at least one battery and can comprise a cam operating a valve of said container holding volatile substances.

According to a second aspect, the method for diffusing volatile substances by means of a device for diffusing volatile substances described above is characterized in that it comprises the steps of:
- detecting data from at least one of the components of the device;
- analyzing said data to determine the period of time during which diffusion is performed according to said data; and
- diffusing said volatile substances during said period of time determined according to said data.

Preferably, the data that is detected comprises the voltage and/or current applied to the diffusion means of said device, and/or the remaining charge in said at least one battery of the device, calculating its expected service life.

Yield and efficiency are improved with the device and method according to the present invention, dispensing the desired product amount and reducing consumption of the batteries as much as possible, with the subsequent positive impact on the economic expense and on the environmental impact.

BRIEF DESCRIPTION OF THE DRAWINGS

To better understand the preceding description a set of drawings is attached in which a practical embodiment is schematically depicted by way of non-limiting example.

DETAILED DESCRIPTION OF THE INVENTION

Figure 1:
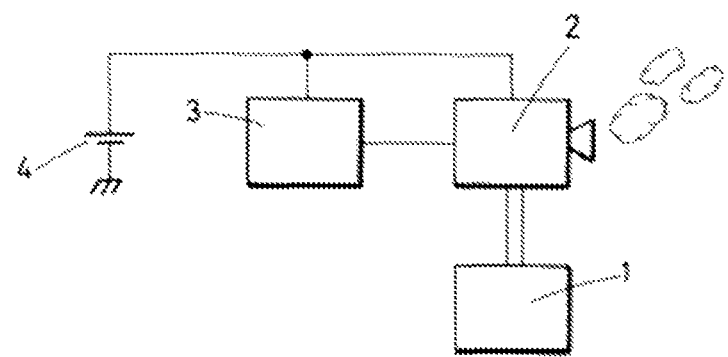
FIG. 1 is a block diagram depicting the basic components of the device of the present invention.

FIG. 1 shows a block diagram depicting the basic components of the device for diffusing volatile substances according to the present invention.

This device comprises a container 1 for the volatile substances, diffusion means 2 diffusing said volatile substances, electronic and/or electric control means 3, the operation of which will be explained below, and one or more batteries 4 powering said diffusion means 2 and said control means 3.

Said control means 3 detect data from the surrounding area and/or from at least one of the components of the device, process or treat this data and make the diffusion means 2 diffuse the volatile substances during a period of time determined according to said detected data. This period of time will be suitable for optimizing the consumption of the battery or batteries 4.

In this way, for example, the control means 3 measure, detect and/or acquire the level of electric voltage applied on the diffusion means 2 (for example, on a motor 5 of said diffusion means) and determine the time during which said diffusion means 2 will be activated, therefore assuring that only the energy required for metering out the desired amount of volatile substance in the environment is applied and used.

In another embodiment, for example, the control means 3 measure, detect and/or acquire the level of instantaneous current applied, such that it detects the time that the diffusion means will short-circuit, no longer applying energy, so the correct and exact amount for metering out the volatile substance in the environment is applied.

Said control means 3 can also detect data from the surrounding area, such as the presence of a person or whether it is light or dark, the presence of bad odors, etc.

Something else that the control means 3 can take into account is the charge of the battery or batteries 4 to determine the time during which said diffusion means 2 will be activated, and also the expected service life of the battery or batteries 4.

It should be indicated that the diffusion means 2 can be any conventional diffusion means, by means of heating to evaporation, by means of spraying, nebulizing, atomizing or other forms.

Figure 2:
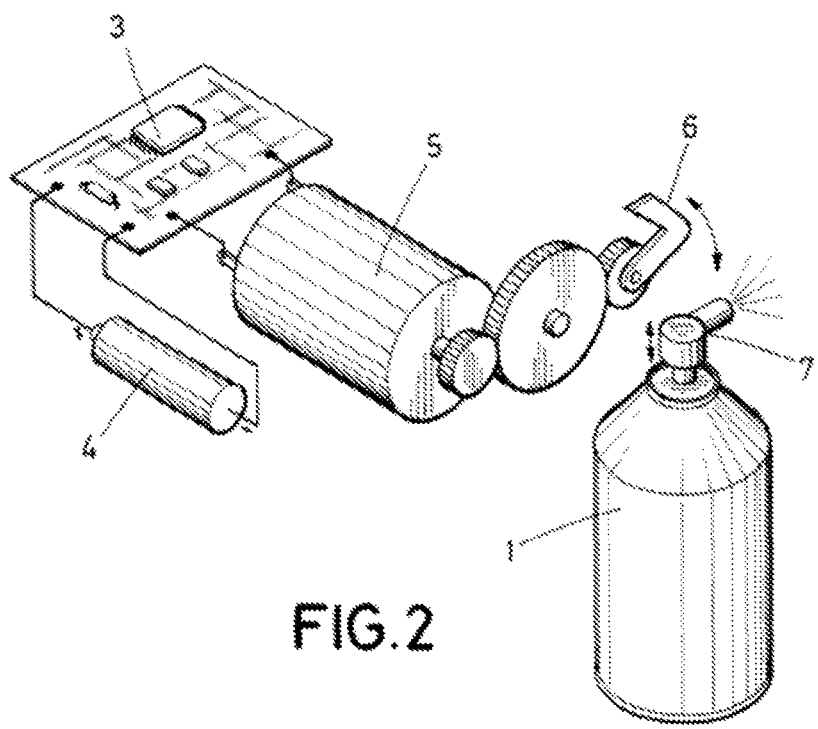
FIG. 2 is a schematic view of the device of the present invention according to a currently preferred embodiment.

However, to provide a complete description of the device according to the present invention, FIG. 2 depicts a possible non-limiting embodiment of said diffusion means 2.

According to this embodiment, the diffusion means 2 comprise a motor 5 connected to said battery or batteries 4 and to said control means 3, the motor 5 of which, by means of a suitable transmission, operates a cam 6 that presses a valve 7 of said container 1, causing the diffusion of the volatile substance into surrounding area during the time the motor 5 operates said cam 6.

According to a second aspect, the present invention also relates to a method for diffusing volatile substances, comprising the steps of:
- detecting data from the surrounding area and/or from at least one of the components of the device;
- analyzing said data to determine the period of time during which diffusion is performed according to said data; and
- diffusing said volatile substances during said period of time determined according to said data.

Figure 3:
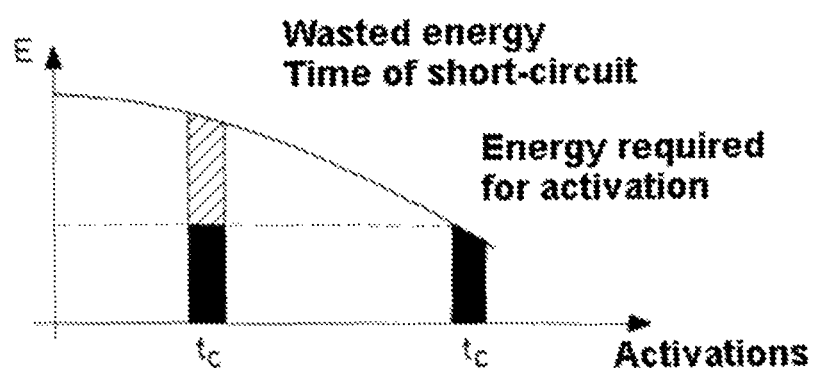
FIG. 3 is a graph of an example of the conventional operation of devices for diffusing volatile substances with conventional batteries.
Figure 4:
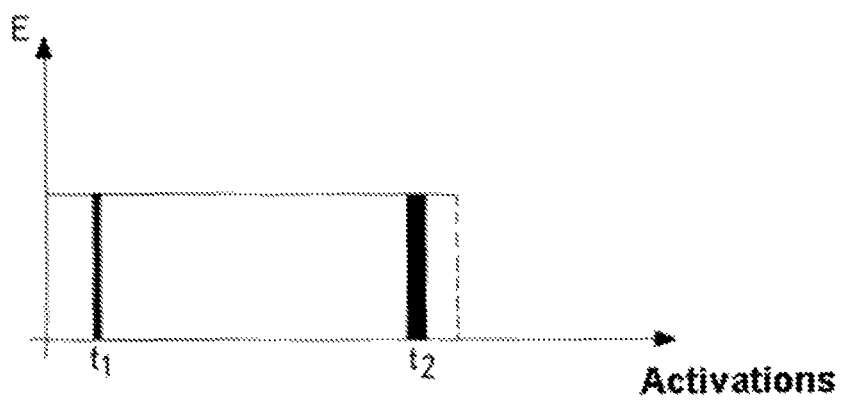
FIG. 4 is a graph of an example of the operation of the device for diffusing volatile substances according to the present invention.

To demonstrate the consumption advantages provided by the present invention, FIGS. 3 and 4 show two graphs of the energy consumption over time.

In both cases, the X-axis indicates time, while the Y-axis indicates energy.

FIG. 3 shows how constant activation pulses that are pre-determined ex factory for the worst-case conditions of the surrounding area are used in conventional diffusion systems, by means of a time $t_c$ assuring that the metering will be performed in any condition. Given that the energy applied is a function of the electric voltage, the electric current and time, when the cells have a maximum voltage value, the energy applied is much greater than what is required, whereas when the cells are almost out of charge, the pulse generates just the energy required for metering out the desired amount.

FIG. 4 shows how the control means can detect, measure, acquire and process the working conditions of the metering means in the device of the present invention, therefore having the data required to adjust the activation pulse width for supplying energy, getting the energy used to be constant and just the right amount required for diffusing the desired metered amount of volatile substance.

Despite having made reference to a specific embodiment of the invention, it is obvious for a person skilled in the art that the device for diffusing volatile substances described is susceptible to a number of variations and modifications, and that all the mentioned details can be replaced with other technically equivalent details without departing from the scope of protection defined by the attached claims.

What is claimed is:

1. A device for diffusing volatile substances, comprising:
   a container for said volatile substances;
   a diffuser configured to diffuse said volatile substances;
   at least one battery configured to supply energy to said diffuser; and
   a controller configured to detect data from at least one of components of the device and determine a period of time during which said at least one battery supplies energy to said diffuser according to said data,
   wherein the controller is configured to measure an energy level of the battery, and adjust a level of the energy supplied to the diffuser from said at least one battery according to the measured energy level of the battery, and
   wherein the diffuser keeps diffusing said volatile substances when the level of the energy supplied to the diffuser is adjusted by the controller such that a desired amount of said volatile substances is kept being diffused by the diffuser in an environment even when the energy level of the battery becomes lower than a predetermined energy level,
   wherein the controller is configured to measure a correct and exact amount of current level applied to the diffuser such that the correct and exact amount of the current level for metering out the volatile substances in the environment is applied to the diffuser.

2. The device for diffusing the volatile substances according to claim 1, wherein said controller detects a voltage applied to the diffuser.

3. The device for diffusing the volatile substances according to claim 1, wherein said controller detects a remaining charge in said at least one battery, and calculates an expected service life of said at least one battery.

4. The device for diffusing the volatile substances according to claim 1, wherein said controller is an electronic and/or electric controller.

5. The device for diffusing the volatile substances according to claim 1, wherein said diffuser comprises a motor connected to said at least one battery.

6. The device for diffusing the volatile substances according to claim 1, wherein said diffuser comprises a cam operating a valve of said container holding the volatile substances.

7. The device for diffusing the volatile substances according to claim 1, wherein the controller is configured to detect a period of time until the diffuser short-circuits.

8. A method for diffusing the volatile substances by using the device according to claim 1, comprising:
   detecting said data from at least one of the components of the device;
   analyzing said data to determine the period of time during which diffusion is performed according to said data; and
   diffusing said volatile substances during said period of time determined according to said data.

9. The method for diffusing the volatile substances according to claim 8, wherein the detected data comprises data relating to a voltage and/or current applied to the diffuser of said device.

10. The method for diffusing the volatile substances according to claim 8, wherein the detected data comprises data relating to a remaining charge in said at least one battery of the device calculating an expected service life of said at least one battery.

* * * * *